United States Patent [19]

Schroeder et al.

[11] Patent Number: 5,693,341
[45] Date of Patent: Dec. 2, 1997

[54] AFFINITY BOUND COLLAGEN MATRICES FOR THE DELIVERY OF BIOLOGICALLY ACTIVE AGENTS

[75] Inventors: Jacqueline A. Schroeder, Redwood City; Hanne Bentz, Newark; Trudy D. Estridge, Fremont, all of Calif.

[73] Assignee: Collagen Corporation, Palo Alto, Calif.

[21] Appl. No.: 405,320

[22] Filed: Mar. 16, 1995

[51] Int. Cl.$^6$ .......................... A61K 47/36; A61K 97/42
[52] U.S. Cl. .......................... 424/488; 514/777; 514/801
[58] Field of Search .......................... 424/484, 486, 424/488

[56] References Cited

U.S. PATENT DOCUMENTS

| | | | |
|---|---|---|---|
| 4,760,131 | 7/1988 | Sundsmo et al. | 530/356 |
| 4,950,483 | 8/1990 | Ksander et al. | 424/422 |
| 5,024,841 | 6/1991 | Chu et al. | 424/422 |
| 5,100,668 | 3/1992 | Edelman et al. | 424/484 |
| 5,110,604 | 5/1992 | Chu et al. | 424/484 |
| 5,206,023 | 4/1993 | Hunziker | 424/422 |
| 5,219,576 | 6/1993 | Chu et al. | 424/484 |
| 5,270,300 | 12/1993 | Hunziker | 514/12 |
| 5,368,858 | 11/1994 | Hunziker | 424/423 |

OTHER PUBLICATIONS

Edelman et al., "Controlled and Modulated Release of Basic Fibroblast Growth Factor", *Biomaterials*, vol. 12, Sep. (1991).

McCaffrey et al., "Transforming Growth Factor–$\beta$ Activity Is Potentiated by Heparin Via Dissociation of the Transforming Growth Factor–$\beta\alpha_2$–Macroglobulin Inactive Complex", *The Journal of Cell Biology*, vol. 109, pp. 441–448 (1989).

Murray et al., "A Micro Sustained Release System for Epiderman Growth Factor", *In Vitro*, vol. 19, No. 10, 743–748 (1993).

Gospodarowicz et al., "Heparin Protects Basic and Acidic FGF from Inactivation", *Journal of Cellular Physiology*, 128:475–484 (1984).

*Primary Examiner*—Peter F. Kulkosky
*Attorney, Agent, or Firm*—Wilhelmus J. Wytenburg; Laurie A. Axford; Kathi Rafayko

[57] ABSTRACT

Affinity bound collagen matrices for the delivery of biologically active agents, and methods for preparing such matrices, are disclosed. A preferred method for preparing the matrices of the invention comprises mixing a binding ligand and an active agent together, allowing the resulting binding ligand-active agent mixture to form an affinity bound complex, then combining the resulting affinity bound complex with collagen to form a matrix. Particular affinity bound matrices comprising collagen, heparin, and an active agent are also disclosed, as well as methods for using the matrices of the invention for delivery of biologically active agents.

8 Claims, 7 Drawing Sheets

AFFINITY BOUND COLLAGEN MATRICES FOR THE DELIVERY OF BIOLOGICALLY ACTIVE AGENTS

FIELD OF THE INVENTION

This invention relates to affinity bound collagen matrices for the delivery of biologically active agents. More particularly, this invention relates to improved processes for preparing affinity bound matrices comprising collagen, a binding ligand, and an active agent.

BACKGROUND OF THE INVENTION

Although most growth factors are very potent, they are rapidly cleared in vivo, as described by Gospodorowicz et al. (J. Cell. Phys., 1984, 128:475–84). Controlled studies of the action of growth factors in vitro on cells and in vivo in laboratory animals have been hampered due to the instability of growth factors both in vivo and in vitro. For example, transforming growth factor beta-2 (TGF-$\beta$2) has a half-life of less than one hour in PBS at 37° C., depending upon the concentration of the TGF-$\beta$2. The solution in which the TGF-$\beta$ is suspended or dissolved may cause destabilization of the active agent (e.g., by aggregation and precipitation). Furthermore, for dilute solutions of TGF-$\beta$, adsorption of the agent to the walls of the vessel may provide an important route for loss of material.

The development of an effective delivery vehicle is important for successful administration of growth factors. Such delivery vehicles are often tailored to serve roles such as desired active agent release profiles, vehicle biocompatability, vehicle bioabsorption and clearance time, and the like. Other primary roles of a useful delivery system are the stabilization and protection of the active agent.

Previous efforts at incorporating active agents (such as growth factors) within a sustained release vehicle have focused on the use of matrix-type delivery systems using solvent casting with hydrophobic polymers such as ethylene vinyl acetate (EVA) copolymer or polylactide/glycolic acid copolymers, as described by Murray et al. (In Vitro, 1983, 19:743–8), Gospodorwicz et al. (J. Cell. Phys., 1984, 128:475–84), and Edelman et al. (Biomaterials, Vol. 12, pp. 619–626, 1991).

Hunziker (U.S. Pat. Nos. 5,206,023; 5,270,300; and 5,368,858) discloses alternative sustained release systems which employ matrix materials such as fibrinogen, collagen, Sepharose, and gelatin.

Chu et al. (U.S. Pat. Nos. 5,024,841; 5,110,604; and 5,219,576) disclose collagen implants useful as wound healing matrices which also serve as an effective sustained delivery system for bioactive agents. Chu et al. disclose a five-step process for preparing such implants (at column 2) and indicate that bioactive agents may be added either while forming fibrillar collagen or immediately after forming fibrillar collagen. Example 5 therein describes the preparation of a collagen/heparin implant containing TGF-$\beta$1 by first mixing TGF-$\beta$1 with collagen-in-solution, separately mixing heparin and collagen-in-solution, and finally combining the TGF-$\beta$1-collagen and heparin-collagen mixtures. Examples 5–7 of Chu et al. disclose collagen-heparin-TGF-$\beta$1 formulations with heparin to TGF-$\beta$1 (weight:weight) ratios of about 5:1 to about 30:1 heparin: TGF-$\beta$.

Ksander et al. (U.S. No. Pat. No. 4,950,483, a CIP U.S. Pat. No. 5,024,841, issued to Chu et al.) disclose collagen sponge compositions comprising collagen, heparin, and TGF-$\beta$, which are prepared in a manner analagous to Chu et al. and which employ the same heparin: TGF-$\beta$1 ratios as Chu et al.

Sundsmo et al. (EP 243179B1; U.S. Pat. No. 4,760,131) disclose improved wound healing compositions comprising reconstituted fibrillar collagen; 0.1% to 10% weight (based on collagen) of heparin or heparin-like glycosaminoglycan; and an effective amount of at least one chemotactic, growth, or differentiation factor (such as FGF, PDGF, EGF, TGF-$\alpha$, TGF-$\beta$, and CTAP-III). These compositions are prepared by first mixing fibrillar collagen and heparin, and subsequently adding the active agent.

Thus, two general methods are known in the art for preparing collagen-binding ligand-active agent matrices. One method involves first mixing the binding ligand (such as heparin) and collagen together, and subsequently adding the active agent (such as TGF-$\beta$) to the binding ligand-collagen mixture. The other method involves mixing all three components (for example, heparin, collagen, and TGF-$\beta$) together simultaneously.

To date, a method for preparing collagen-binding ligand-active agent matrices which involves first mixing the binding ligand and the active agent and subsequently adding collagen has not been disclosed. The absence of such a method is probably due to the fragility (e.g., instability) and high cost of purified or recombinantly produced active agents, such as TGF-$\beta$, which have historically been the last component to be added to a composition. By adding the active agent to the formulation last, the amount of manipulation, and thus the risk loss of activity of the active agent, is reduced. The skilled artisan working with active agents, such as TGF-$\beta$, would not be motivated to prepare a composition using a method wherein the active agent is involved in the first or early steps of production, due to the inherent risks involved in further, often intensive, manipulation of the composition.

In sharp contrast, the methods of the present invention involve first combining a binding ligand, such as heparin, with an active agent, such as TGF-$\beta$, and allowing the mixture to affinity bind. The resulting binding ligand-active agent (e.g., heparin-TGF-$\beta$) affinity bound complex is subsequently admixed with collagen (e.g., fibrillar collagen). There are no harsh conditions (such as heat or organic solvents) in contact with the growth factor during the manufacture of the formulation.

Glycosaminoglycan molecules have been found to bind biologically significant macromolecules. Heparin not only binds, but stabilizes and protects macromolecules (see, for example, McCaffrey et al., J. Cell Biol., Vol. 109, pp. 441–448). By pre-incubating the TGF-$\beta$ with heparin and allowing the formation of an affinity bound complex, we have found that the TGF-$\beta$ has much greater stability and a lifetime of at least 2 months at 37° C. The surprising and unexpected discovery that the heparin-TGF-$\beta$ affinity bound complex can be maintained at physiological pH without irrevocable loss of activity allows for easier processing and manufacture of TGF-$\beta$-containing compositions. We have also shown that affinity bound TGF-$\beta$2-heparin can be subjected to further manipulation (such as moderate heating), or combined with other materials (such as collagen), without irrevocable loss of activity.

Collagen is a naturally occurring biopolymer whose normal function is to provide strength and integrity to tissue; it also provides an environment for cell proliferation and differentiation. By adding collagen to the heparin-TGF-$\beta$ affinity bound complex, useful physical (e.g., consistency, injectability, etc.), chemical, and biological (e.g., bioabsorption) properties may be introduced or adjusted. TGF-β is generally cleared from the administration site by binding with other molecules, such as alpha-2-macroglobulin. The addition of collagen to the matrix prevents or retards the active (e.g., biological) and/or passive (e.g., diffusional) dissipation of the TGF-β away from the administration site, thereby enhancing the intended therapeutic effects, such as regrowth of local tissue.

While heparin forms affinity bound complexes with TGF-β, heparin also forms affinity bound complexes with collagen. A mixture prepared by simultaneously combining collgen, heparin, and TGF-β necessarily reflects the competition between both collagen and TGF-β for heparin. By pre-incubating the TGF-β with heparin prior to adding collagen, substantially smaller quantities of heparin are needed to achieve the same final TGF-β content obtained by either of the other known methods for preparing such matrices. For example, the methods of the present invention permit the use of heparin to TGF-β (weight:weight) ratios of about 0.01:1 to about 5:1 heparin: TGF-β; more preferably, about 2:1 heparin:TGF-β. In contrast, known methods (such as those disclosed by Chu et al.) typically employ larger relative amounts of heparin, i.e., heparin to TGF-β (weight:weight) ratios greater than about 5:1 heparin:TGF-β.

The improved methods of this invention thus permit the use of substantially lower heparin to TGF-β (weight:weight) ratios, which ratios could not be employed by other known methods. Similarly, the affinity bound matrices prepared by the improved methods of this invention contain overall a substantially reduced amount of binding ligand (e.g., heparin). This reduced amount of heparin provides an important practical advantage, as heparin itself, in larger quantifies, is biologically active. By reducing the amount of heparin required to affinity bind a given amount of active agent (e.g., TGF-β), and thus reducing the overall heparin content of the composition, the biological effects of heparin can be minimized or removed. That is, in the affinity bound matrices of the invention, the role of heparin as a carrier dominates its role as an active agent.

All publications cited above and herein are incorporated herein by reference to describe and disclose the subject matter for which it is cited.

SUMMARY OF THE INVENTION

The present invention pertains to a method of preparing an affinity bound collagen-binding ligand-active agent matrix comprising mixing a binding ligand with an active agent to prepare a binding ligand-active agent mixture, maintaining the binding ligand-active agent mixture under conditions suitable to allow the formation of a binding ligand-active agent affinity bound complex, then adding collagen to the binding ligand-active agent mixture. According to a particularly preferred method of the invention, heparin is mixed with an active agent to prepare a binding ligand-active agent mixture, the heparin-active agent mixture is maintained under conditions suitable to form a heparin-active agent affinity bound complex, then collagen is added to the heparin-active agent mixture to prepare an affinity bound collagen-heparin-active agent matrix.

Also provided by the invention are affinity bound matrices comprising collagen, heparin, and an active agent, wherein the heparin and the active agent are present in a weight ratio of between about 0.01:1 to about 5:1 heparin to active agent.

DETAILED DESCRIPTION OF THE PREFERRED EMBODIMENTS OF THE INVENTION

A. The Affinity Bound Matrices

Figure 1:
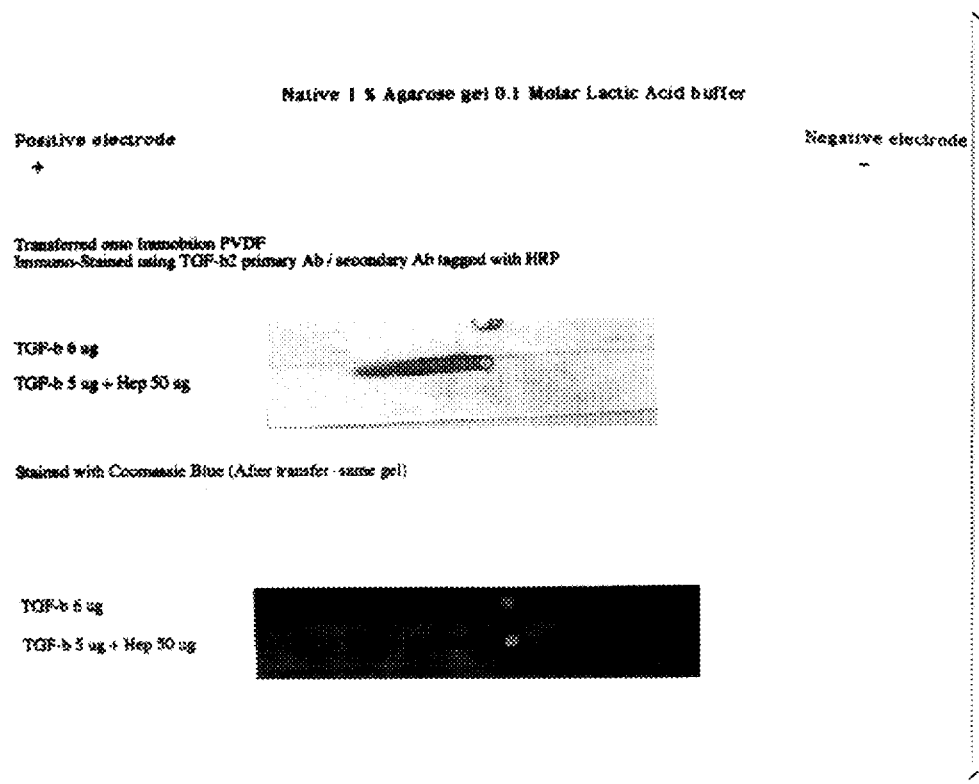
FIG. 1 shows agarose gel electrophoresis of 6 μg of TGF-β2 alone and 5 μg of TGF-β2 affinity bound to 50 μg of heparin.

The present invention relates to improved methods for the preparation of affinity bound matrices comprising collagen, a binding ligand, and an active agent.

The term "collagen" as used herein is used in the conventional sense to describe a material which is the major protein component of the extracellular matrix of bone, cartilage, skin, and connective tissue in animals. Collagen in its native form is typically a rigid, rod-shaped molecule approximately 300 nanometers (nm) long and 1.5 nm in diameter. It is comprised of three collagen polypeptides which form a tight triple helix. The collagen polypeptides are characterized by a long midsection having the repeating sequence -Gly-X-Y-, where X and Y are often proline or hydroxypro line, bounded at each end by the "telopeptide" regions, which constitute less than about 5 percent (%) of the molecule. The telopeptide region of the collagen chains are typically responsible for the crosslinking between chains and for the immunogenicity of the protein.

In general, collagen from any source may be used to prepare the compositions of the present invention; for example, collagen may be extracted and purified from human or other mammalian source, such as bovine or porcine corium and human placenta, or may be recombinantly or otherwise produced. The preparation of purified, substantially non-antigenic collagen in solution from bovine skin is basically a three-step process involving solubilization, enzyme (e.g., pepsin) treatment, and purification, as described in U.S. Pat. Nos. 4,140,537 and 4,488,911 which are incorporated herein by reference. Commonly owned allowed U.S. patent application Ser. No. 07/921,810 now U.S. Pat. No. 5,428,022 discloses methods of extracting and purifying collagen from the human placenta. Commonly owned, copending U.S. application Ser. No. 08/183,648 discloses methods of producing recombinant human collagen in the milk of transgenic animals, including transgenic cows. The term "collagen" or "collagen material" as used herein refers to all forms of collagen, including those which have been processed or otherwise modified.

Collagen of any type, including, but not limited to, types I, II, III, IV, or any combination thereof, may be used, although type I is generally preferred. Either atelopeptide or telopeptide-containing collagen may be used; however, when collagen from a xenogeneic source, such as bovine collagen, is used, atelopeptide collagen is generally preferred, because of its reduced immunogenicity compared to telopeptide-containing collagen.

Fibrillar collagen is the matrix material of choice for use in preparing the compositions of the invention because its biocompatability has been well characterized and because it is the major component of the extracellular matrix. The extracellular matrix serves as a storage site for growth factors, as described by Bashkin et al. (Biochem., 1989, 28:1737–48) and Flaumenehaft et al. (J. Cell. Phys., 1989, 140:75–81). In addition, the extracellular matrix may serve to modulate growth factor activity by acting as a reservoir and then releasing the factor into the surrounding tissue. Therefore, collagen admixed with a heparin-bound growth factor is a delivery system which mimics the natural state of growth factors.

Collagen for use in the practice of the invention is preferably noncrosslinked, fibrillar collagen present in aqueous suspension. Noncrosslinked atelopeptide fibrillar collagen is commercially available from Collagen Corporation (Palo Alto, Calif.) at collagen concentrations of 35 mg/ml and 65 mg/ml under the trademarks Zyderm® I Collagen and Zyderm II Collagen, respectively.

The term "binding ligand" as used herein refers to organic molecules which form affinity bound complexes with active agents. Examples of various binding ligands include, without limitation, heparin, binding proteins (such as BP3), hyaluronic acid, collagen types IV and V, wheat germ, fibronectin, decorin, biglycan, proteoglycan and betaglycan. Preferred binding ligands are heparin, heparin-like compounds (for example, betaglycans, syndocans, and integrins), hepaxin-containing compounds, and compounds having heparin-like binding affinities. Particularly preferred binding ligands are heparin, heparan sulfate, and subspecies of heparin and other polyanionic carbohydrates such as fucoidan and dextran sulfate.

Heparin is the most preferred binding ligand for use in preparing the affinity bound matrices of the present invention. A well-known glycosaminoglycan, heparin is made up of repeating disaccharide units comprising a derivative of an amino sugar possessing negatively charged carboxylate and sulfate groups. Heparin has been widely used for its affinity binding properties, particularly in heparin-modified columns for use in chromatographic isolation or purification (so-called "heparin-affinity chromatography"), as available from Pierce, Sigma, and BioRad, among others. For example, Heparin-Sepharose® CL-6B can be purchased from Pharmacia Fine Chemicals; AHi-Gel heparin gel Catalog No. 153-6173, from BioRad; HiTrap heparin column 5-4836 or SigmaChrom™ HPLC column #Z29,002-5, from Sigma; immobilized heparin #20207, from Pierce.

The preferred binding ligand, heparin, has been shown to form affinity bound complexes with a number of active agents, including without limitation: antithrombin III; Factors VII, IX, XI, XII, and XIIa; thrombin; properdin; complements C1, C2, C3, and C4; complement factor B; C3b inactivator; Gc globulin; protein HC; fibronectin; β2-glycoprotein 1; C-reactive protein; lipoprotein lipase; hepatic triglyceride lipase; VLDL, LDL; VLDL apoprotein; HDLP; restriction endonucleases; RNA polymerase; RNA polymerase I and II; DNA polymerase; DNA ligase; polynucleotide kinase; elongation factor (EF-1); initiation factors; protein synthesis factors; ribosomes; estrogen receptor; androgen receptor; platelet factor 4; SV 40 tumor antigen; Hepatitis B surface antigen; hyaluronidase; collagenase inhibitor; neurophysin; trehalose phosphate synthetase. Heparin is also known to form affinity bound complexes with the following agents: transforming growth factor beta (TGF-β), fibroblast growth factor (FGF), platelet-derived growth factor (PDGF), epidermal growth factor (EGF), osteogenin, insulin-like growth factors (IGFs), vascular endothelial growth factor, granulocyte/macrophage colony-stimulating factor (CSF), gamma interferon, glia-activating factors, and collagen type V.

The term "biologically active agent" or "active agent" as used herein refers to organic molecules which exert biological effects in vivo. Examples of active agents include, without limitation, enzymes, receptor antagonists or agonists, hormones, growth factors, antibiotics, antimicrobial agents, and antibodies. The term "active agent" is also intended to encompass various cell types which can be delivered to a tissue site via the matrices of the invention, which will be discussed further below. The term "active agent" is also intended to encompass combinations or mixtures of two or more active agents, as defined above.

Preferred active agents for use in the present invention include members of the transforming growth factor (TGF) supergene family, such as the beta transforming growth factors (for example, TGB-β1, TGB-β2, TGB-β3), bone morphogenic proteins (for example, BMP-1, BMP-2, BMP-3, BMP-4, BMP-5, BMP-6, BMP-7, BMP-8, BMP-9), Inhibins (for example, Inhibin A, Inhibin B), growth differentiating factors (for example, GDF-1), Activins (for example, Activin A, Activin B, Activin AB). Particularly preferred active agents are the transforming growth factors (TGFs), such as TGF-β1, TGF-β2, and TGF-β3.

Members of the TGF supergene family are multifunctional regulatory proteins. For example, TGF-β2, a 25,000 molecular weight homodimeric peptide, is capable of inducing site-specific healing responses by increasing collagen synthesis and deposition, as well as remodeling at sites of soft tissue repair. TGF-β2 also activates osteoblasts to synthesize collagen in vitro. The most abundant sources of TGF-β2 are bone and platelets.

The term "affinity bound complex" is used herein in the conventional sense to refer to an association of two or more molecules, wherein the association is effected by virtue of intermolecular and/or intramolecular forces (such as hydrogen bonding or van der Waals forces), as opposed to covalent bonding.

Affinity bound complexes may be characterized by the dissociation constant, $K_d$. Suitable affinity bound complexes will have a small enough $K_d$ so that sufficient quantities of the complex are formed and remain in the bound state, but not so small that complex formation is effectively irreversible. For example, for an affinity bound complex, AB, formed from two species A and B, the $K_d$ is often approximated as $K_d=[A][B]/[AB]$, wherein the square brackets denote molar concentrations of the respective species. For such two-species complexes, suitable affinity bound complexes will preferably have $K_d$ values more than about $10^{-15}$ M and less than about $10^{-3}$ M; more preferably, more than about $10^{-12}$ M and less than about $10^{-6}$ M; most preferably, more than about $10^{-10}$ M and less than about $10^{-7}$ M.

Many affinity bound complexes are formed via a general interaction between the constituent molecules, while many others are formed via a "lock-and-key" interaction, reflecting a high degree of specificity. Common examples of affinity bound complexes include enzyme-substrate complexes, receptor-ligand complexes, antibody-antigen complexes, and the like.

The term "affinity bound matrix" or "affinity bound composition" as used herein refers to compositions comprising, at the minimum, collagen, a binding ligand component, and an active agent component, wherein at least a portion of the binding ligand component is affinity bound to at least a portion of the active agent component In addition, a portion of the binding ligand component, the active agent component, and/or the binding-ligand-active agent complex component may further be affinity bound to the collagen.

B. Formation of the Affinity Bound Matrices

In accordance with the methods of the invention, a binding ligand and an active agent are mixed (for example, by combining the binding ligand and active agent together in an Eppendorf tube, then vortex mixing the contents of the tube) and the resulting binding ligand-active agent mixture is allowed to incubate for a sufficient amount of time to form a binding ligand-active agent affinity bound complex.

In accordance with a preferred method of the invention, heparin and an active agent are mixed and the resulting heparin-active agent mixture is allowed to incubate at a temperature within the range of about 0° C. to about 8° C. for a minimum of about 24 hours; preferably, for a period of about 24 hours to about 96 hours. The exact amount of time required to form the heparin-active agent affinity bound complex is dependent upon the particular active agent employed and the temperature at which the heparin-active agent mixture is incubated, i.e., lower incubation temperatures require longer incubation times, higher incubation temperatures require shorter incubation times. We have found that a minimum of about 48 hours incubation time is needed to effect formation of the affinity bound heparin-active agent complex when an incubation temperature of 4° C. is used. Lower incubation temperatures, such as within the range of about 0° C. to about 4° C., are generally preferred, as higher incubation temperatures can lead to loss of activity of the active agent.

Preferably, the heparin and the active agent are present in a weight ratio of between about 0.01:1 to about 5:1 heparin to active agent (e.g., 0.01–5 µg of heparin per 1 µg of active agent); most preferably, about 2:1 heparin to active agent (e.g., 2 µg of heparin per 1 µg of active agent).

Following formation of the affinity bound complex, the binding ligand-active agent mixture is combined with collagen, which is generally in aqueous suspension at a concentration of between about 3 to about 120 mg/ml; preferably, between about 15 mg/ml to about 80 mg/ml. The mount of collagen suspension employed is dependent upon the desired final concentration of the active agent, but is generally within the range of between about 0.1 cc to about 5 cc. The binding ligand-active agent mixture and collagen can be combined using syringe-to-syringe mixing techniques.

By incubating the active agent with the binding ligand to form a binding ligand-active agent complex, then containing the resulting complex within a collagen matrix, the active agent benefits from stabilized or increased local concentration, modulation of the agent's interaction with other agents present within the body, alteration of the agent's rate of diffusion through the collagen matrix, and protection against proteolytic degradation.

The term "stabilization" as used herein refers to retention of the activity of an active agent, such that the period of time in which the agent remains active is prolonged or extended. Stability of an active agent is generally measured using various in vitro test methods, such as cell culture methods, or by in vivo testing.

The term "potentiation" as used herein refers to enhancement of the activity of an active agent. Potentiation is best measured using various in vivo testing methods.

The term "modulation" as used herein refers to the ability to vary the proliferation, synthesis, metabolism, or other characteristics of living cells in vitro or in vivo, and can be measured by cellular response in in vitro and in vivo tests. The term "modulation" is also used to refer to the ability to vary the rate of release, dose, or other characteristic of the active agent to the tissue site of administration, as measured in vivo.

The term "depot delivery" or "localized delivery" as used herein refers to the delivery of an active agent which is contained to a specific area or site. Depot delivery can be determined by in vivo retention of local activity over time, such as in the rat subcutaneous model.

The term "sustained release" or "controlled release" as used herein refers to a constant dosage of active agent over time. Sustained release of an active agent can be determined by in vivo release of the active agent over time, such as in the rat subcutaneous model.

USE AND ADMINISTRATION

The affinity bound collagen-binding ligand-active agent matrices of the present invention can be used to deliver biologically active agents in their native and active forms to various sites within the body of a patient in order that the active agent can exert a local therapeutic effect at the site of administration. As used herein, the term "patient" is intended to encompass all mammalian patients, preferably human patients.

The affinity bound matrices containing an active agent can be injected (usually through an 18-gauge or smaller needle; preferably, a 22-gauge or smaller needle; most preferably, a 25-gauge or smaller needle) or otherwise implanted directly to the tissue site in need of the agent's particular therapeutic effect, such that said therapeutic effect is concentrated locally, where it is needed, and not systemically throughout the entire body. As such, the matrices of the invention provide for depot delivery of an active agent to the site of administration and controlled release of the active agent to that site over time.

The matrices of the present invention can also be used to deliver various types of cells to a desired site of administration in order to form new tissue. For example, mesenchymal stem cells can be delivered to produce cells of the same type as the tissue into which they are delivered. Mesenchymal stem cells are not differentiated and therefore can differentiate to form various types of new cells due to the presence of an active agent or the effects (chemical, physical, etc.) of the local tissue environment Examples of mesenchymal stem cells include osteoblasts, chondrocytes, and fibroblasts. Osteoblasts can be delivered to the site of a bone defect to produce new bone; chondrocytes can be delivered to the site of a cartilage defect to produce new cartilage; fibroblasts can be delivered to produce collagen wherever new connective tissue is needed; neurectodermal cells can be delivered to form new nerve tissue; epithelial cells can be delivered to form new epithelial tissues, such as liver, pancreas, etc.

As described in the Examples below, growth factors such as TGF-β can be delivered via the matrices of the invention to the site of a soft or hard tissue defect. The healing response induced by the local delivery of TGF-β2 is directly related to the predominant cell type present at the tissue site. For example, the predominant cell type present in soft tissue is the fibroblast. Therefore, when TGF-β2 is delivered to a soft tissue site, the tissue response induced by the presence of the TGF-β2 is activation of fibroblasts which, upon activation, produce extracellular matrix materials, particularly, neocollagen. However, when TGF-β2 is delivered to the site of a hard tissue defect, such as a broken bone, osteoblasts are activated, resulting in a cascade of events leading to new bone formation.

EXAMPLES

The following examples are put forth so as to provide those of ordinary skill in the an with a complete disclosure and description of how to make the preferred embodiments of the conjugates, compositions, and devices and are not intended to limit the scope of what the inventors regard as their invention. Efforts have been made to ensure accuracy with respect to numbers used (e.g., amounts, temperature, molecular weight, etc.) but some experimental errors and deviation should be accounted for. Unless indicated otherwise, parts are parts by weight, molecular weight is weight average molecular weight, temperature is in degrees Centigrade, and pressure is at or near atmospheric.

Example 1

Preparation of Collagen-Heparin-TGF-β2 Affinity Bound Matrix

Ten (10) mg of heparin (available from Hepar Industries, Franklin, Ohio) was dissolved in 1.0 ml of phosphate-buffered saline (PBS; 0.02M, 0.09% NaCl, pH 7.4). The resulting 10 mg/ml heparin solution was sterile-filtered through a 0.22 micron filter (available from Millipore Corporation, Bedford, Mass.).

One (1) mg of TGF-β2 (available from Celtrix Pharmaceuticals, Santa Clara, Calif.) was dissolved in 1.0 ml of acidic ethanol. Six hundred (600) μl of the resulting 1 mg/ml TGF-β2 solution was combined with 300 μl of the 10 mg/ml heparin solution (to achieve a final weight ratio of 5:1 heparin: TGF-β2) in an Eppendorf tube and then mixed by vortexing. The resulting heparin-TGF-β2 mixture was stored at 4° C.

After storage for at least 2 days at 4° C., the heparin-TGF-β2 mixture was mixed using syringe-to-syringe mixing with 15 cc of atelopeptide fibrillar bovine dermal type I collagen having a collagen concentration of 35 mg/ml (Zyderm® I Collagen, available from Collagen Corporation, Palo Alto, Calif.).

Example 2

Evaluation of Binding in Collagen-Heparin-TGF-β2 Affinity Bound Matrix

Electrophoresis under native conditions was carried out to evaluate binding of TGF-β2 to heparin in formulations containing various molar ratios of TGF-β2 to heparin. The agarose gel (1% wt/vol in water) was allowed to gel in a horizontal gel mold and sample wells were manually cut into the gel. Tank buffer was 0.1M lactic acid buffer in water, pH 2. Running conditions were constant voltage (200 V) for 2 hours at 4° C. Gels were either stained with Coomassie Blue R-250 or transferred to nitrocellulose and incubated with mouse anti-TGF-β (2,3) monoclonal antibody (available from Genzyme Corporation, Framingham, Mass.), followed by peroxidase-labeled anti-mouse IgG (available from Zymed Laboratories, Inc., South San Francisco, Calif.).

Figure 2:
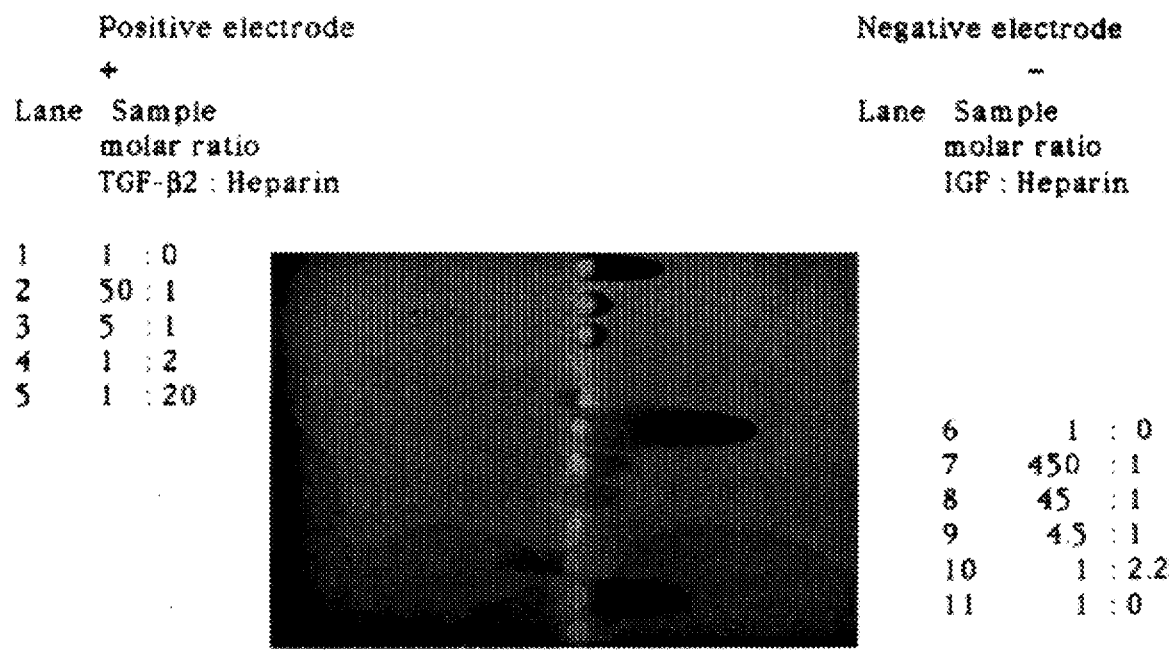
FIG. 2 shows agarose gel electrophoresis of TGF-β2 with heparin in molar ratios of 1:0, 50:1, 5:1, 1:2, and 1:20 TGF-β2 to heparin.

When a protein binds to heparin, which has a highly negative overall charge, the protein will move with the heparin toward the cathode. TGF-β2 has an overall positive charge and, when electrophoresed alone, migrates toward the anode, as shown in FIG. 1. As shown in FIG. 2, increased amounts of heparin cause the TGF-β2 to migrate from the negative electrode to the positive electrode, indicating that there is affinity binding between the TGF-β2 and the heparin.

Fibrillar collagen was heparinized according to the procedure described by Senatore et. al (J. Biomed Mater. Res., 24:939–57) to evaluate binding of TGF-β2 to heparinized collagen in comparison to non-heparinized fibrillar collagen. Thirty-one (31) milligrams of heparinized fibrillar collagen, 31 mg of (non-heparinized) fibrillar collagen, and 0.41, 0.62, and 1.24 μg of TGF-β2 were applied to nitrocellulose by suction using BioDot SF microfiltration apparatus (available from BioRad Laboratories, Richmond, Calif.). The non-occupied binding sites were blocked with 3% (wt/vol) bovine serum albumin (BSA) in PBS for 30 minutes at 37° C.

The nitrocellulose with immobilized TGF-β2 (positive control), heparinized collagen, and fibrillar collagen was incubated overnight at 4° C. in a solution of TGF-β2 (1.0 mM TGF-β2 in 1% wt/vol BSA/PBS). After incubation, the nitrocellulose was washed in PBS three times and incubated with mouse anti-TGF-β (2,3) monoclonal antibody, followed by peroxidase-labeled anti-mouse IgG. The peroxidase label was visualized by TMB peroxidase substrate (available from Kirkegaard & Perry Laboratories, Inc., Gaithersburg, Md.).

Figure 3:
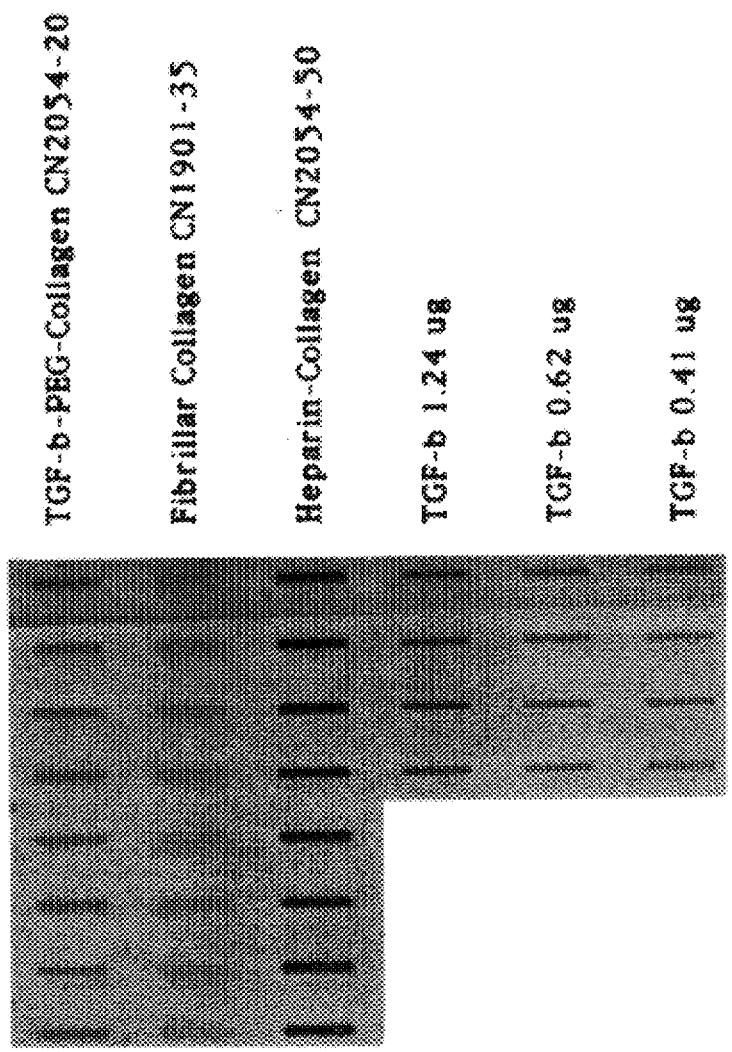
FIG. 3 shows affinity binding of TGF-β2 to heparinized fibrillar collagen and nonheparinized fibrillar collagen using a modified Dot Blot technique.

As shown in FIG. 3, non-heparinized fibrillar collagen does not significantly bind TGF-β2, as compared to heparinized fibrillar collagen. This is is evidence of affinity binding of the growth factor to heparinized collagen.

Example 3

In vitro Evaluation of Bioactivity of Collagen-Heparin-TGF-β2 Affinity Bound Matrix The bioactivity of TGF-β2 was measured by its ability to inhibit mink lung epithelial cell (ATCC-MvILu CCl-64) proliferation, according to the method described by Tada et al. (J. Immunol., 1991, 146:1077–182). Cellular inhibitory response was measured using a chromogenic substrate for acid phosphatase. A quantitative estimate of TGF-β2 activity was determined by the inhibition of proliferation of mink lung epithelial cells by comparison to a standard curve of TGF-β2. Formulations were tested for activity by diluting the formulation directly in the tissue culture media.

Formulations comprising 0.1, 0.01, and 0.001 mg/ml heparin in PBS were prepared. Formulations comprising 1 μg/ml TGF-β2 in 0.01, 0.01, and 0.001 mg/ml heparin in PBS were also prepared. TGF-β2 at a concentration of 1 μg/ml in acidic ethanol was used as the positive control.

Figure 4:
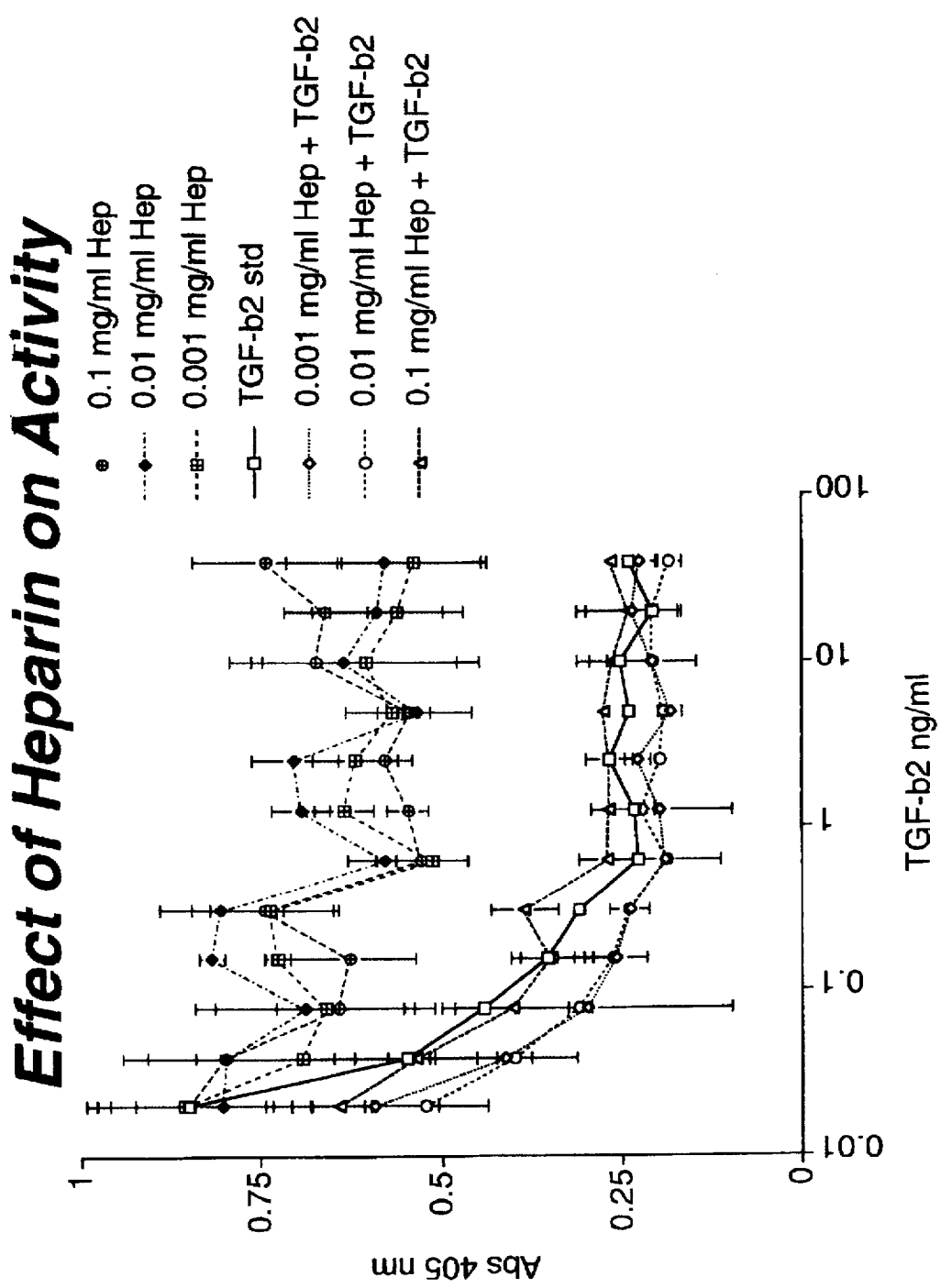
FIG. 4 compares the bioactivity of formulations comprising 0.1, 0.01, and 0.001 mg/ml heparin in PBS, and 1 μg/ml TGF-β2 in 0.01, 0.01, and 0.001 mg/ml heparin in PBS, as measured using the mink lung epithelial cell inhibition assay.

As shown in FIG. 4, the formulations containing heparin alone without TGF-β2 allowed mink lung epithelial cell proliferation, as indicated by high absorbance values in the acid phosphatase assay. All formulations containing TGF-β2 displayed a decrease in absorbance values as the concentration of TGF-β2 increased, indicating enhanced inhibition of mink lung epithelial cell proliferation.

Bioactivity of the collagen-heparin-TGF-β2 affinity bound matrix (containing 35 mg/ml collagen, 200 μg/ml heparin, and 40 μg/ml TGF-β2) was evaluated using the mink lung epithelial cell inhibition assay described above, and compared to formulations containing 35 mg/ml fibrillar collagen and 200 μg/ml heparin with no TGF-β2 (collagen-heparin), and 35 mg/ml fibrillar collagen admixed with 40 μg/ml TGF-β2 (collagen-TGF-β2 admixture). Fresh TGF-β2 at a concentration of 40 μg/ml in acidic ethanol was used as the positive control.

Figure 5:
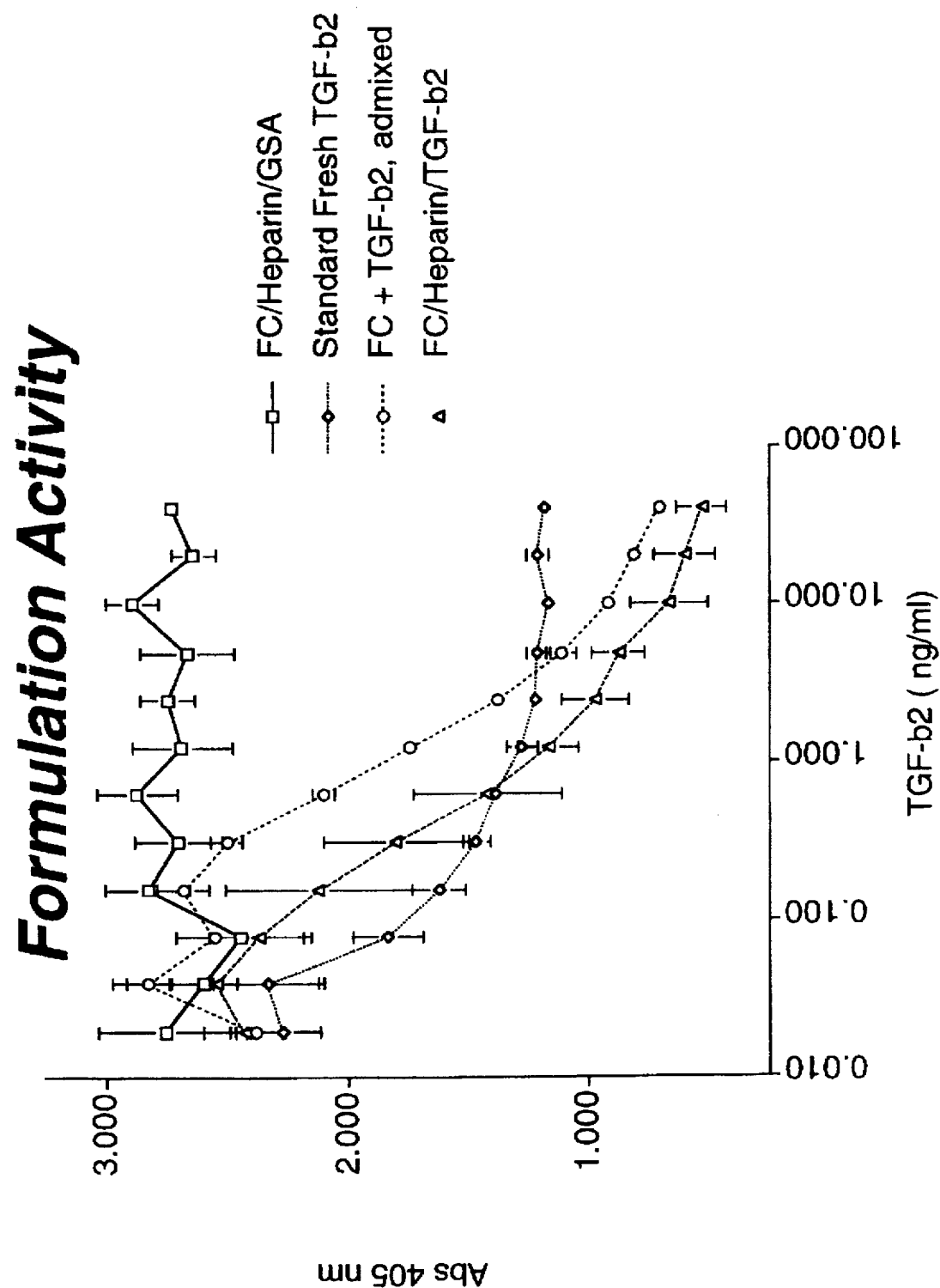
FIG. 5 compares the bioactivity of the collagen-heparin-TGF-β2 affinity bound matrix with a collagen-TGF-β2 admixture and collagen-heparin with no TGF-β2, as measured using the mink lung epithelial cell inhibition assay. The collagen-heparin-TGF-2 matrix and the collagen-TGF-β2 admixture contained 1 μg/ml TGF-β2.

As shown in FIG. 5, all formulations containing TGF-β2 inhibited proliferation of mink lung epithelial cells. The collagen-heparin-TGF-β2 matrix showed slightly better inhibition of mink lung epithelial cell proliferation than the collagen-TGF-β2 admixture for the same TGF-β2 concentration.

Example 4

In vitro Evaluation of Stability of Collagen-Heparin-Bound TGF-β2

The stability of heparin-bound TGF-β2 was evaluated by binding 1 μg of TGF-β2 to 2 μg of heparin in 1 ml of PBS. Non-bound TGF-β2 was diluted into PBS in the same manner as the heparin-bound TGF-β2 and used as the negative control. The samples were incubated at 37° C. Samples were tested for activity in the mink lung epithelial cell inhibition assay (described in Example 3, above) after 24 hours and 2 months incubation at 37° C. and compared to a positive control consisting of freshly prepared TGF-β2 in acidic ethanol.

Figure 6:
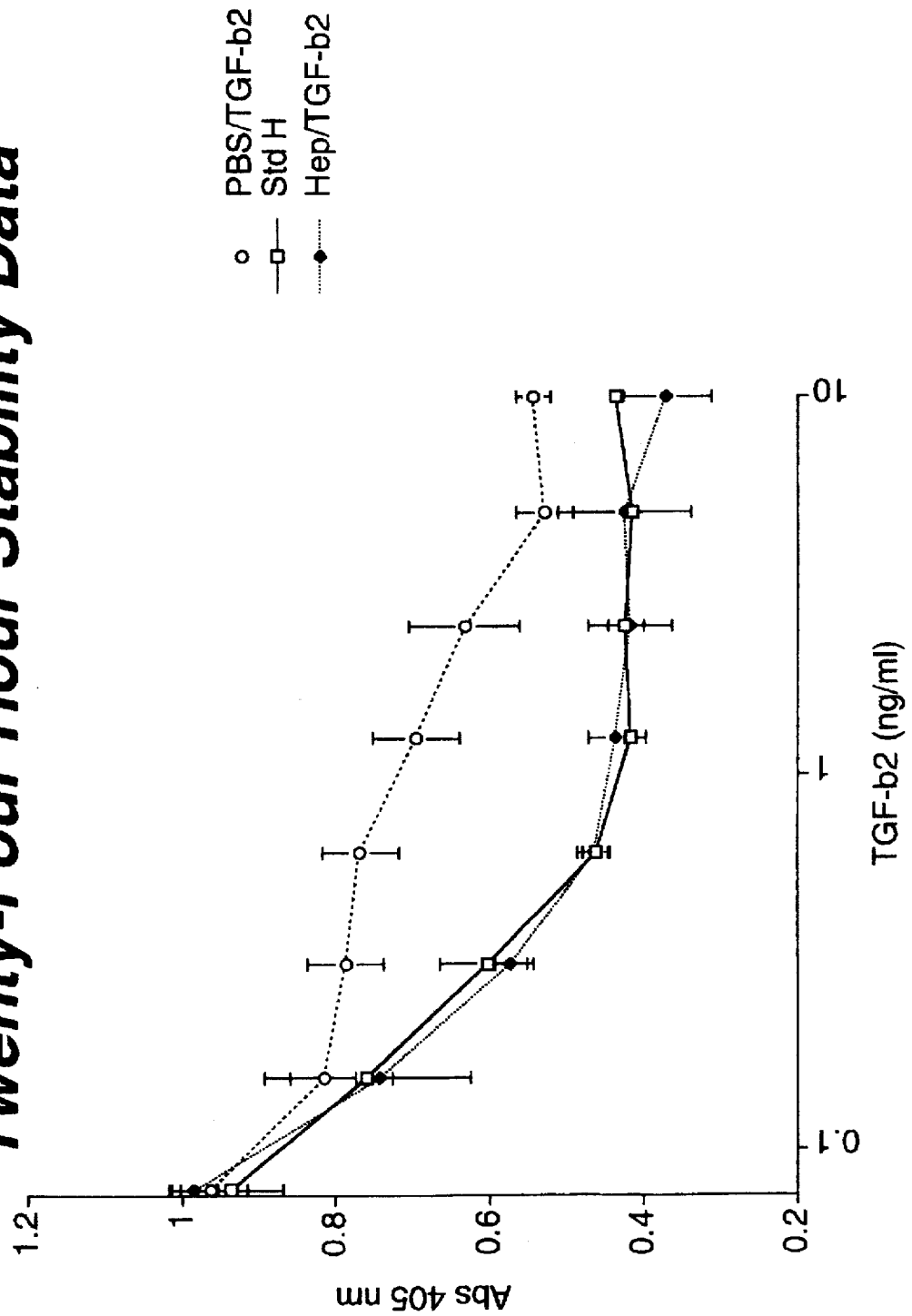
FIG. 6 compares the bioactivity of heparin-bound TGF-β2 in PBS and non-bound TGF-β2 in PBS after 24 hours incubation at 37° C., as measured using the mink lung epithelial cell inhibition assay.
Figure 7:
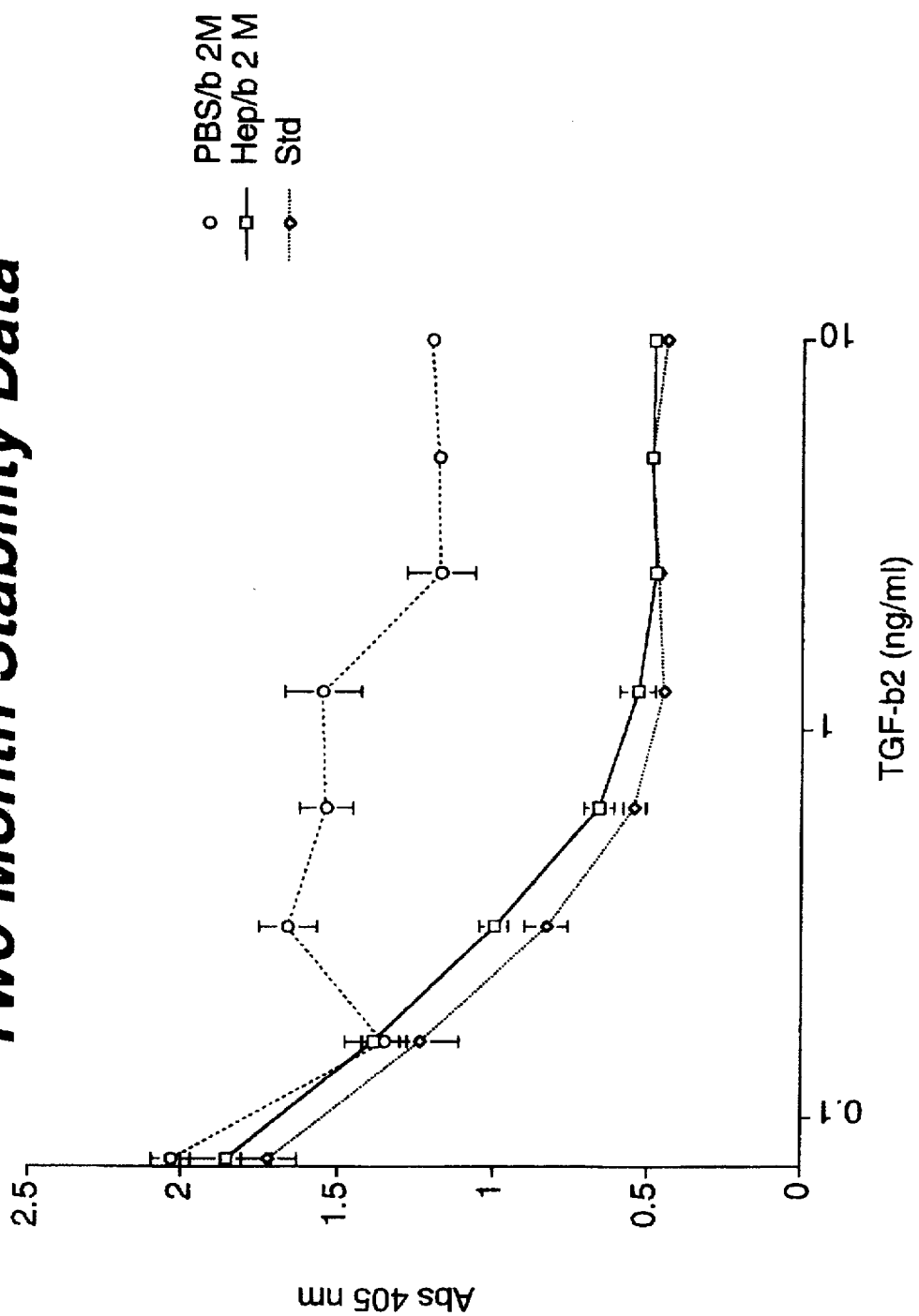
FIG. 7 compares the bioactivity of heparin-bound TGF-β2 in PBS and non-bound TGF-β2 in PBS after 2 months incubation at 37° C., as measured using the mink lung epithelial cell inhibition assay.

As shown in FIGS. 6 and 7, non-bound TGF-β2 in PBS loses activity within 24 hours, while hepaxin-bound TGF-β2 in PBS remains active after 2 months. After 2 months incubation at 37° C., there is a dramatic difference in the activity of the non-bound TGF-β2 in PBS compared to the heparin-bound TGF-β2 in PBS. The non-bound TGF-β2 lost activity, while the heparin-bound TGF-β2 retained its activity, which was similar to the freshly prepared TGF-β2 positive control.

Example 5

In vivo Evaluation of Activity of Collagen-Heparin-TGF-β2 Affinity Bound Matrix in the Rat Subcutaneous Model The collagen-heparin-TGF-β2 affinity bound matrix, prepared as described in Example 1, was evaluated in the rat subcutaneous model to establish soft tissue biocompatibility and in vivo activity. Controls were fibrillar collagen alone and fibrillar collagen admixed with TGF-β2 (collagen-TGF-β2 admixture).

Fifteen Sprague-Dawley rats in each of the three groups received a bolus injection consisting of 0.2 ml, 8 μg TGF-β2, on each side of their dorsal subcutaneous area. Five animals of each group were sacrificed and the implants removed 7, 21, and 42 days following implantation. Explants with surrounding tissue were fixed with 10% neutral buffered formalin. After fixation, the explants were sectioned and mounted on slides, which were subsequently stained using trichrome and hematoxylin/eosin.

At day 7, the implants containing the collagen-heparin-TGF-β2 matrix and the collagen-TGF-β2 admixture showed responses consisting of recruitment, alignment, and activation of fibroblasts, resulting in the deposition of new collagenous connective tissue. Implants containing the fibrillar collagen control material were observed to be non-reactive, displaying a typical response to fibrillar collagen.

At day 21, implants containing the collagen-heparin-TGF-β2 affinity bound matrix displayed greater activity (activated fibroblasts) than implants containing the collagen-TGF-β2 admixture. By day 42, the implants containing the collagen-heparin-TGF-β2 matrix were much denser than the implants containing either the fibrillar collagen control or the collagen-TGF-β2 admixture. The collagen-heparin-TGF-β2 retained their bolus shape and remained intact, compared to implants containing the fibrillar collagen control and the collagen-TGF-β2 admixture, both of which had started to be degraded by the host and to flatten out.

Example 6

In vivo Evaluation of Activity of Collagen-Heparin-TGF-β2 Affinity Bound Matrix in the Rat Parietal Model The collagen-heparin-TGF-β2 affinity bound matrix, prepared as described in Example 1, was evaluated in the rat parietal model to determine bioactivity of TGF-β2 in a bony site. Controls were fibrillar collagen alone and fibrillar collagen admixed with TGF-β2 (collagen-TGF-β2 admixture).

Six Sprague-Dawley rats in each of the three groups received two implants, one for each defect in the parietal bone. Each implant contained 1.0 to 2.0 μg TGF-β2 per defect. Three animals of each group were sacrificed and the implants removed 28 and 56 days following implantation. Explants with surrounding tissue were fixed with 10% neutral buffered formalin and partially decaldried. A cross-sectional area at the center of each defect was taken and processed using routine histologic methods. Five-millimeter sections of the defect were stained with hematoxylin and eosin.

Histological examination of the parietal defect sites evaluated bone ingrowth and closure of the parietal defect. Sites that received the collagen-heparin-TGF-β2 affinity bound matrix healed by bony ingrowth from the margins of the skull defect. At 56 days post-implantation, defects containing the collagen-heparin-TGF-β2 matrix were completely closed in three out of three animals, and were similar histologically to the bone of the adjacent normal bone. In comparison, implant sites containing the fibrillar collagen control and the collagen-TGF-β2 admixture formed bony union in only one of three animals by day 56.

What is claimed is:

1. A method of preparing an affinity bound matrix comprising collagen, a polyanionic carbohydrate, and a positively charged biologically active protein, said method comprising, in order, the steps of:

(i) mixing the polyanionic carbohydrate with the positively charged biologically active protein in the absence of collagen to prepare a polyanionic carbohydrate-positively charged biologically active protein mixture;

(ii) maintaining said polyanionic carbohydrate-positively charged biologically active protein mixture for a sufficient length of time in the absence of collagen under conditions suitable to form a polyanionic carbohydrate-positively charged biologically active protein affinity bound complex; and (iii) admixing said polyanionic carbohydrate-positively charged biologically active protein affinity bound complex with collagen under conditions suitable to form said affinity bound matrix;

wherein said positively charged biologically active protein is more stable in said affinity bound matrix than an equivalent affinity bound matrix formed without a first step of mixing said polyanionic carbohydrate with said positively charged biologically active protein in the absence of collagen.

2. The method of claim 1, wherein the polyanionic carbohydrate is selected from the group consisting of: heparin, heparin-like compounds, heparin-containing compounds, and compounds having heparin-like binding affinities.

3. The method of claim 2, wherein the polyanionic carbohydrate is heparin.

4. A method of preparing an affinity bound matrix comprising collagen, heparin, and a positively charged biologically active protein, said method comprising, in order, the steps of:

(i) mixing the heparin with the positively charged biologically active protein in the absence of collagen to prepare a heparin-positively charged biologically active protein mixture; and (ii) maintaining said heparin-positively charged biologically active protein mixture for a sufficient length of time in the absence of collagen under conditions suitable to form a heparin-positively charged biologically active protein affinity bound complex; and (iii) admixing said heparin-positively charged biologically active protein affinity bound complex with collagen under conditions suitable to form said affinity bound matrix;

wherein said biologically active protein is more stable in said affinity bound matrix than an equivalent affinity bound matrix formed without a first step of mixing said polyanionic carbohydrate with said biologically active protein in the absence of collagen.

5. The method of claim 1 or 4, wherein the positively charged biologically active protein is in the transforming growth factor supergene family.

6. The method of claim 5, wherein the positively charged biologically active protein is transforming growth factor beta.

7. The method of claim 4, wherein the heparin-positively charged biologically active protein mixture is incubated at a temperature within the range of about 0° C. to about 8° C. for a minimum of about 24 hours.

8. The method of claim 4, wherein the heparin and the positively charged biologically active protein are present in the affinity bound matrix in a weight ratio of between about 0.01:1 to about 5:1 heparin to active agent.

* * * * *